(12) United States Patent
Cohen et al.

(10) Patent No.: US 9,327,144 B2
(45) Date of Patent: May 3, 2016

(54) POWDER COMPOSITIONS CONTAINING EDIBLE GRAINS

(75) Inventors: Kenneth Cohen, Thornhill (CA); David Singh, Scarborough (CA)

(73) Assignee: ELC Management LLC, New York, NY (US)

( * ) Notice: Subject to any disclaimer, the term of this patent is extended or adjusted under 35 U.S.C. 154(b) by 634 days.

(21) Appl. No.: 12/403,922

(22) Filed: Mar. 13, 2009

(65) Prior Publication Data

US 2010/0233110 A1    Sep. 16, 2010

(51) Int. Cl.
| | |
|---|---|
| *A61K 8/36* | (2006.01) |
| *A61K 8/29* | (2006.01) |
| *A61Q 17/04* | (2006.01) |
| *A61Q 19/00* | (2006.01) |
| *A61K 8/02* | (2006.01) |
| *A61K 8/97* | (2006.01) |

(52) U.S. Cl.
CPC ............... *A61Q 19/00* (2013.01); *A61K 8/022* (2013.01); *A61K 8/29* (2013.01); *A61K 8/97* (2013.01); *A61Q 17/04* (2013.01)

(58) Field of Classification Search
CPC ........... A61K 8/022; A61K 8/29; A61K 8/97; A61Q 19/00; A61Q 17/04
See application file for complete search history.

(56) References Cited

U.S. PATENT DOCUMENTS

| | | | |
|---|---|---|---|
| 3,215,724 A | 11/1965 | Strobel et al. | |
| 3,781,417 A | 12/1973 | Welter et al. | |
| 4,014,995 A | 3/1977 | Juliano et al. | |
| 5,498,412 A | 3/1996 | Fujie | |
| 5,658,579 A | 8/1997 | LaFleur et al. | |
| 5,776,476 A | 7/1998 | Billmers et al. | |
| 5,925,380 A | 7/1999 | Roulier et al. | |
| 6,171,602 B1 | 1/2001 | Roman | |
| 6,416,788 B1 | 7/2002 | Barr | |
| 2004/0086474 A1* | 5/2004 | Rabe et al. | 424/63 |
| 2005/0112078 A1 | 5/2005 | Boddupalli et al. | |
| 2006/0034876 A1* | 2/2006 | Cheney et al. | 424/401 |
| 2006/0257436 A1* | 11/2006 | Kaminuma et al. | 424/401 |
| 2007/0020209 A1 | 1/2007 | Zamyatin et al. | |
| 2007/0269537 A1* | 11/2007 | Gupta | 424/740 |
| 2008/0175803 A1 | 7/2008 | Gordon | |

FOREIGN PATENT DOCUMENTS

| | | | |
|---|---|---|---|
| EP | 0182295 | * | 11/1985 |
| KR | 20050077092 | | 8/2005 |
| KR | 1020050077092 | * | 8/2005 |

OTHER PUBLICATIONS

PCT International Search Report; International Application No. PCT/US2009/037464; Completion Date: Apr. 13, 2010; Date of Mailing: Apr. 14, 2010.
PCT Written Opinion of the International Searching Authority, or the Declaration; International Application No. PCT/US2009/037464; Completion Date: Apr. 13, 2010; Mailing Date: Apr. 14, 2010.
http://www.gnpd.com; Mintel gnpd; White Face Powder; Record ID: 617726; Vitapharm; Viva; Colour Cosmetics; Face Colour Cosmetics—Powder; Indonesia; Nov. 2006.
http://www.gnpd.com; Mintel gnpd; Refreshing Body Powder; Record ID: 951392; Origins Natural Resources; Origins Organics; Skincare; Body Care; USA; Jul. 2008.
http://www.gnpd.com; Mintel gnpd; Renew & Reveal Facial Cleanser; Record ID: 860029; Bare Escentuals; Bare Escentuals RareMinerals; Skincare; Face/Neck Care; USA; Feb. 2008.
http://www.gnpd.com; Mintel gnpd; Translucent Base; Record ID: 1004334; Aubrey Organics; Aubrey Organics Silken Earth; Colour Cosmetics; Face Colour Cosmetics—Foundations / Fluid Illuminators; USA; Nov. 2008.
http://www.gnpd.com; Mintel gnpd; Gentle Mineral Blush; Record ID: 1024876; Procter & Gamble; CoverGirl TruBlend MicroMinerals; Colour Cosmetics; Face Colour Cosmetics—Blush; UK; Dec. 2008.
http://www.gnpd.com; Mintel gnpd; 100% Natural Mascara; Record ID: 1055962; Physicians Formula; Physicians Formula Organic Wear Colour Cosmetics; Eye Colour Cosmetics Eye-Lash; USA; Feb. 2009.
http://www.gnpd.com; Mintel gnpd; Foundation; Record ID: 1021512; Procter & Gamble; CoverGirl TruBlend MicroMinerals; Colour Cosmetics; Face Colour Cosmetics—Foundations / Fluid Illuminators; USA; Dec. 2008.
http://www.gnpd.com; Mintel gnpd; Pressed Face Powder; Record ID: 882320; N.Y.C. New York Colour; N.Y.C. New York Color; Colour Cosmetics; Face Colour Cosmetics—Powder; South Africa; Mar. 2008.
http://www.gnpd.com; Mintel gnpd; Shineless Loose Powder; Record ID: 895488; Sally Hansen; Sally Hansen Cornsilk; Colour Cosmetics; Face Colour Cosmetics—Powder; USA; Apr. 2008.
http://www.gnpd.com; Mintel gnpd; Pressed Powder: Record ID: 964109; Proceter & Gamble; CoverGirl CG Smoothers; Colour Cosmetics; Face Colour Cosmetics—Powder; Canada; Aug. 2008.
http://www.gnpd.com; Mintel gnpd; Naturally Luminous Blush; Record ID: 846027; Procter & Gamble; CoverGirl TruBlend; Colour Cosmetics; Face Colour Cosmetics—Blush; USA; Jan. 2008.
http://www.gnpd.com; Mintel gnpd; Powder Blush; Record ID: 1004349; Aubrey Organics; Aubrey Organics Silken Earth: Colour Cosmetics; Face Colour Cosmetics—Blush; USA; Nov. 2008.
http://www.accessdata.fda.gov/scripts/cdrh/cfdocs/cfcfr/CFRSearch.cfm?CFR Part=701&..; U.S. Food & Drug Administration (FDA); § 701.1—Misbranding; Code of Federal Regulations; Title 21; vol. 7; 21CFR701; pp. 1-18; Apr. 1, 2008.
CCOF Manual 2: USDA Natural Organic Program Standards; Subpart A—Definitions; pp. 1-33; Dec. 12, 2007.
Related Application; PCT/US2008/069323; Method & Compositions for Treating Skin; Filing Date: Jul. 7, 2008; Claiming Priority from U.S. Appl. No. 61/015,250; First Inventor: Collins, et al.
21 CFR Ch. 1 (Apr. 1, 2006 Edition); §347.3-347.20; Jun. 4, 2003.
http://www.gnpd.com; Mintel gnpd; Liquid Baby Powder; Record ID: 1033265; Nature's Care; Manufacture P/L; Mei Mei; Skincare; Body Care; Australia; Jan. 2009.

* cited by examiner

*Primary Examiner* — Johann R Richter
*Assistant Examiner* — Genevieve S Alley
(74) *Attorney, Agent, or Firm* — Julie Blackburn

(57) ABSTRACT

A powder composition comprising a particulate phase containing a plurality of edible grains.

13 Claims, No Drawings

POWDER COMPOSITIONS CONTAINING EDIBLE GRAINS

TECHNICAL FIELD

The invention is in the field of compositions for application to skin in powder form or powder compositions for use in formulating other cosmetic products in liquid, solid, or semi-solid form that may be anhydrous or aqueous based.

BACKGROUND OF THE INVENTION

Cosmetics consumers are becoming more interested in purchasing and using cosmetic products with ingredients that are referred to as "organic" or "natural". It is the consumer perception that such ingredients or products containing those ingredients are manufactured using more environmentally friendly processes, are biodegradable, and are more natural on skin and/or hair. While the plain meaning of the term "organic" means a compound that contains carbon atoms, when used in conjunction with materials, processes, and products it means that such items are manufactured and maintained in a way that meets certain standards. For example ingredients referred to as organic generally must avoid use of chemical inputs such as fertilizer, pesticides, antibiotics, food additives, genetically modified organisms, or irradiation; must be cultivated from farmland that has been free from chemicals for a number of years; where detailed written production and sales records are maintained with respect to cultivation, production and sale; and where strict physical separation between organic and non-certified organic products is maintained; and where the manufacturer agrees to undergo periodic on-site inspections.

It has very desirable to formulate cosmetics from naturally derived, non-synthetic ingredients. Such compositions may also contain one or more ingredients that are certified organic, or if not organic they may be natural. Some examples of natural ingredients are naturally derived grains that are often used as food sources. One preferred embodiment is a color cosmetic composition containing such naturally derived grains.

SUMMARY OF THE INVENTION

The invention comprises a powder composition with SPF comprising a particulate phase containing a plurality of edible grains.

The invention also comprises a powder composition comprising a particulate phase containing a plurality of edible grains and at least one botanical anti-oxidant.

The invention also comprises a powder composition comprising a particulate phase containing a plurality of edible grains and at least one vitamin.

The invention further comprises a non-comedogenic or non-acnegenic powder composition comprising a plurality of edible grains.

The invention further comprises an OTC skin protectant powder composition comprising at least one OTC monograph approved skin protectant and a plurality of edible grains.

The invention further comprises a powder composition containing a plurality of edible grains and at least one skin whitening ingredient.

The invention further comprises a powder composition for treating skin irritation, rash, itch, cuts, scrapes, burns, chafing, and windburn comprising a plurality of edible grains and at least two OTC monograph approved skin protectants.

The invention further comprises a method for protecting and relieving undesirable effects of injured or exposed skin or mucous membrane surfaces from harmful or annoying stimuli comprising applying to the skin or mucous membranes a powder composition comprising a plurality of edible grains and at least one skin protectant active ingredient.

DETAILED DESCRIPTION

I. Definitions

All percentages mentioned herein are percentages by weight unless otherwise indicated.

The term "anti-oxidant" means an ingredient that has singlet oxygen scavenging activity, particularly when formulated into topical products that are applied to keratinous surfaces.

The term "certified" when used in connection with the term "organic" means that the organic ingredient or product was certified in accordance with 7 C.F.R. §205.400 et seq., hereby incorporated by reference in its entirety, or Ecocert®, the European control and certification authority.

The term "edible grains" means grains that are traditionally known as food sources, although the particular grain or grains used need not actually be edible.

The term "keratinous surfaces" means skin, hair, or nails.

The term "organic" when used herein means that the ingredient or material complies with 7 C.F.R. §205, hereby incorporated by reference in its entirety, with respect to the preparation, manufacture, disposal, etc.

The term "OTC" means "over the counter" drug as defined in 21 C.F.R. §330.13, that is, a topical non-prescription cosmetic or pharmaceutical product that contains certain active ingredients as defined in 21 C.F.R. §347.3 et seq., both provisions hereby incorporated by reference in their entirety.

The term "powder composition" means that the composition is in the form of a pressed or loose powder.

The term "skin protectant" means a skin protectant active ingredient as set forth in 21 C.F.R. §347.10, hereby incorporated by reference in its entirety.

The term "SPF" means with respect to the composition referred to that it provides protection against UVA or UVB or both types of radiation, by use of either chemical or physical sunscreen ingredients.

II. The Compositions

The compositions may be in the form of a pressed, loose, or liquid powder for application to keratinous surfaces. The powder may be suitable for application to facial skin or lips, or for use on the body. The powder composition may be anhydrous, or may contain water or other non-aqueous polar solvents. The powder composition may be used as a base for the formulation of aqueous or anhydrous products. In the case where the powder composition is used as a base in the formulation of aqueous based products, the powder composition is prepared as the particulate phase and formulated into the aqueous based product (which may be an emulsion or suspension) in the usual manner. The compositions of the invention may be in the form of water in oil or oil in water emulsions, balms, lipsticks or glosses, mascara, foundation, powder, concealer, sunscreens, eyeliner, eye shadow, blush, and so on.

The powder compositions comprise ingredients including but not limited to those set forth herein.

A. Edible Grains

The powder compositions of the invention comprise a plurality of edible grains. The grains are preferably in particulate form and may range from about 0.5 to 100 microns, preferably from about 1-50 microns, more preferably from about 1 to 10 microns in diameter. Preferred are cereal grains, including those from the monocot family Poaceae. In one preferred embodiment the grains either alone or in combination with the other particulates present in the composition have a particle size ranging from about 2 to 5 microns in diameter. The grains are present in the composition ranging from about 0.1 to 99%, preferably from about 0.5 to 95%, more preferably from about 1 to 85%. Examples of such edible grains include, but are not limited to tapioca starch, oat flour, soy, rice, corn, wheat, barley, sorghum, millets, triticale, buckwheat, rye, acorn, almond, amaranth, arrowroot, beans, besan, bran, bulgar, calrose, canola, spelt, quinoa, channa, chestnut, chickpea, coconut, cornmeal, couscous, dal, farina, fava beans, flax, garbanzo, grits, hominy, kudzu, lentils, maize, malt, manioc, milo, peanut, popcorn, saffron, sesame, sunflower seed, urd, and mixtures thereof.

If desired, one or more of the edible grains may be "certified organic" as defined herein. An example of a suitable certified organic particulate includes organic oatmeal, also referred to as oat flour or *Avena Sativa*, one source of which is Allyson Enterprises, Inc., Huntington, N.Y. Tapioca starch is another example of a suitable certified organic particulate, a source of which is National Starch Personal Care, Bridgewater, N.J. A variety of other organic particulates are suitable so long as they are certified as set forth herein.

B. SPF

In one preferred embodiment of the invention the powder composition comprises physical or chemical sunscreens or both which provide UVA or UVB protection or both, also referred to as sun protective factor. If present, amounts ranging from about 0.1 to 75%, preferably from about 0.5 to 70%, more preferably from about 1 to 65% are suitable.

1. UVA Chemical Sunscreens

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds having the general formula

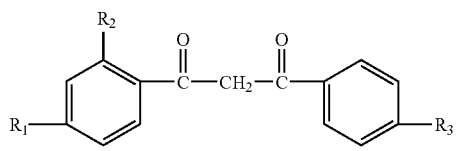

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

Other types of UVA sunscreens include dicamphor sulfonic acid derivatives, such as ecamsule, a sunscreen sold under the trade name Mexoryl™, which is terephthalylidene dicamphor sulfonic acid, having the formula:

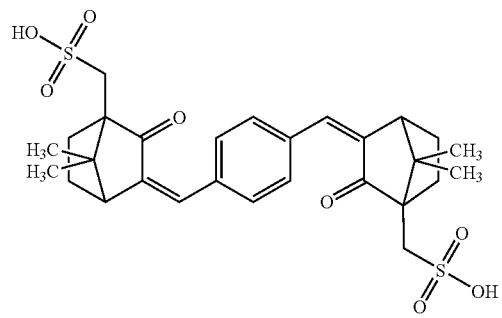 [SMILES: CC1(C)C2CCC1(CS(=O)(=O)O)C(=O)/C2=C\c1ccc(/C=C2\C(=O)C3(CS(=O)(=O)O)CCC2C3(C)C)cc1]

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 110% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

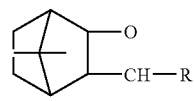

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

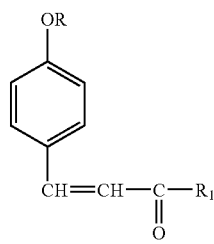

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

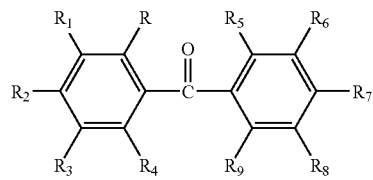

wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

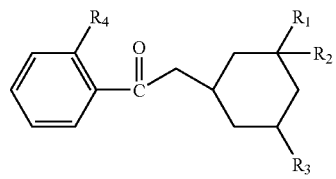

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

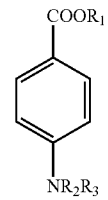

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula: wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have a certain SPF (sun protective factor) values ranging from about 1-50, preferably about 2-45, most preferably about 5-30. Calculation of SPF values is well known in the art.

3. Physical Sunscreens

Also suitable are solid particulates that provide UV protection by acting as solid physical blocks. Examples include titanium dioxide, zinc oxide, and other types of metal oxides. The particle size may range from about 0.000001 to about 100 microns, preferably from about 0.0005 to about 50 microns.

C. Antioxidants

In another embodiment of the invention the composition comprise one or more antioxidants with free radical scavenging activity. If present, suggested ranges are from about 0.00001 to 20%, preferably from about 0.00005 to 18%, more preferably from about 0.0001 to 10% by weight of the total composition. Suitable antioxidants include botanical extracts with antioxidant properties, or antioxidants in the form of chemical compounds or mixtures.

1. Botanical Extracts

Suitable botanical extracts include extracts from plants (herbs, roots, flowers, fruits, seeds) such as flowers, fruits, vegetables, and so on, including yeast ferment extract, *Padina Pavonica* extract, *Thermus Thermophilis* ferment extract, *Camelina Sativa* seed oil, *Boswellia Serrata* extract, olive extract, *Aribodopsis Thaliana* extract, *Acacia Dealbata* extract, *Acer Saccharinum* (sugar maple), acidopholus, acorus, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Siegesbeckia Orientalis, Macrocycstis Pyrifera, Pyrus Malus, Saxifraga Sarmentosa, Vitis Vinifera, Morus Nigra, Scutellaria Baicalensis, Anthemis Nobilis, Salvia Sclarea, Rosmarinus Officianalis, Citrus Medica Limonum, Panax Ginseng, Siegesbeckia Orientalis, Fructus Mume, Ascophyllum Nodosum, Glycine Soja* extract, *Beta Vulgaris, Haberlea Rhodopensis, Polygonum Cuspidatum, Citrus Aurantium Dulcis, Vitis Vinifera, Selaginella Tamariscina, Humulus Lupulus, Hordeum Vulgare, Triticum Vulgare, Citrus Reticulata* Peel, *Punica Granatum, Asparagopsis, Curcuma Longa, Menyanthes Trifoliata, Helianthus Annuus, Hordeum Vulgare, Cucumis Sativus, Evernia Prunastri, Evernia Furfuracea*, and mixtures thereof. Particularly preferred are *Lycium Chinense* extract, *Punica Granatum* extract, or mixtures thereof.

2. Chemical Antioxidants

Also suitable are antioxidants that are chemical compounds or mixtures of compounds or ingredients, including but not limited to, potassium sulfite, sodium bisulfite, sodium erythrobate, sodium metabisulfite, sodium sulfite, propyl gallate, cysteine hydrochloride, butylated hydroxytoluene, potassium sorbate, chlorophenesin, butylated hydroxyanisole, caffeic acid, carnosic acid, carotenoids, and those listed on pages 2755 to 2757 of the C.T.F.A. Cosmetic Ingredient Dictionary and Handbook, Eleventh Edition, 2006, hereby incorporated by reference in its entirety.

D. Vitamins

In another embodiment of the invention the composition contains one or more vitamins or vitamin derivatives. If present, suggested ranges are from about 0.001 to 20%, more preferably from about 0.001 to 10%, more preferably from about 0.005 to 8%. Suitable vitamins or derivatives include, but are not limited to, A, B, C, D, E, K, or alcohol or carboxylic acid derivatives thereof such as ascorbyl palmitate, tocopheryl acetate, ascorbyl tetraisopalmitate, and the like.

E. Skin Protectants

In one embodiment of the invention the composition comprises at least one skin protectant, preferably an OTC monograph approved skin protectant. Suitable skin protectants include allantoin when present in amounts ranging from about 0.5 to 2%; aluminum hydroxide gel when present in amounts ranging from about 0.15 to 5%; calamine when present in amounts ranging from about 1 to 25%; cocoa butter when present in amounts ranging from about 50 to 100%, cod liver oil when present in amounts ranging from about 5 to 14%; colloidal oatmeal either alone when present in an amount of at least 0.003%, or in combination with mineral oil where the oatmeal is present in an amount of at least 0.007%; dimethicone when present in an amount from 1 to 30%; glycerin when present in an amount from 20 to 45%; hard fat when present in an amount ranging from about 50 to 100%; kaolin when present in an amount ranging from about 4 to 20%; lanolin when present in an amount ranging from 12.5 to 50%; mineral oil when present in an amount ranging from 50 to 100%, or from 30 to 35% when present in combination with colloidal oatmeal; petrolatum when present in an amount ranging from 30 to 100%; sodium bicarbonate; starch when present in an amount ranging from 10 to 98%; white petrolatum when present in an amount ranging from 30 to 100%; zinc acetate when present in an amount ranging from 0.1 to 2%; zinc carbonate when present in an amount ranging from 0.2 to 2%; or zinc oxide when present in an amount ranging from 1 to 25%.

F. Other Particulate Materials

The compositions of the invention may contain other particulate materials, which may not be certified organic, in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

1. Powders

The particulate matter may be colored or non-colored (for example white) non-pigmented powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, diatomaceous earth, fuller's earth, glyceryl starch, hectorite, hydrated silica, kaolin (either pigmented or non-pigmented), magnesium aluminum silicate, magnesium trisilicate, maltodextrin, montmorillonite, microcrystalline cellulose, silica, mica, aluminum hydroxide, titanium dioxide, zinc laurate, zinc myristate, zinc rosinate, alumina, attapulgite, calcium carbonate, calcium silicate, dextran, nylon, silica silylate, silk powder, sericite, soy flour, tin oxide, titanium hydroxide, trimagnesium phosphate, or mixtures thereof. The above mentioned powders may be surface treated with lecithin, amino acids, mineral oil, silicone, or various other agents either alone or in combination, which coat the powder surface and render the particles more lipophilic in nature.

Also suitable are particulate materials extracted from fruits and vegetables, which may be colored, including those set forth in U.S. Pat. No. 6,171,602, hereby incorporated by reference in its entirety. Examples include beet powder, radish powder, carmine, coffee, cochineal, cotton seed powder, paprika, turmeric, and so on.

2. Pigments

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

G. Emollients or Skin Conditioning Agents

The composition of the invention may comprise one or more emollients or skin conditioning agents that may be in the liquid, semi-solid, or solid form. The emollients may act as binders for the particulates present, or coat the particulate particles, or provide other beneficial effects such as moisturization, aesthetic feel, and so on. If present, the emollient may range from about 0.01 to 75%, preferably from about 0.05 to 70%, more preferably from about 0.1 to 50% by weight of the total composition. Suitable agents include but are not limited to those set forth herein.

1. Esters

Suitable esters are mono-, di-, and triesters. The composition may comprise one or more esters selected from the group, or mixtures thereof.

(a) Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

(b). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, octyldodecyl stearoyl stearate, and so on.

(c). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

2. Hydrocarbon Oils

Also suitable are various types of hydrocarbon oils such as paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

3. Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, *camelina sativa* oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diisostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

4. Naturally Derived Oils or Waxes

Also suitable are various types of oils or waxes derived from vegetable sources such as plants, trees, roots, fruits, or leaves. Examples include *Butyrosperum Parkii* (Shea butter); carnauba wax, ceresin wax, ozokerite wax, *Persea Gratissima* (Avocado) butter; Rose wax; Safflower oil, tall oil, squalane, almond oil, apricot oil, and the like.

The composition may additionally comprise other ingredients including but not limited to preservatives, film formers, and the like.

The composition may be anhydrous or aqueous based. More preferably the composition is substantially anhydrous, that is it contains less than about 5%, preferably less than about 3%, more preferably less than about 1% water.

H. Anti-Acne Ingredients

In one embodiment of the invention it may be desirable to incorporate one or more anti-acne ingredients into the composition to provide compositions that have anti-acnegenic and, possibly, non-comedogenic properties. If present, suggested ranges are from about 0.001 to 50%, more preferably from about 0.005 to 30%, more preferably from about 0.01 to 20% of the composition. Suitable anti-acne ingredients include salicylic acid, benzoyl peroxide, sulfur, or mixtures thereof.

I. Ingredients for Minimizing Skin Redness, Rash, Itching, and Other Skin Conditions The composition may also contain one or more ingredients that minimize skin redness due to irritation, inflammation, rosacea, or other similar skin conditions. If present, such ingredient may range from about 0.0001 to 25%. Preferred is a botanical blend and method as disclosed in PCT/US2008/069323, filed Jul. 7, 2008, entitled Method and Compositions for Treating Skin, naming co-inventors Donald F. Collins, Daniel H. Maes, and Neelam Muizzuddin and claiming priority from U.S. Provisional Patent Application Ser. No. 61/015,250, filed Dec. 20, 2007, which is hereby incorporated by reference in its entirety.

Such botanical blend is prepared by selecting ingredients that inhibit one or more of the various pathways that contribute to skin irritation and inflammation, specifically, the (1)

Adhesion Pathway, which is the pathway by which cells adhere to blood vessels and other skin tissues when injury or immune challenge has occurred; (2) the Chemotaxis Pathway, which is the pathway where chemical signals cause inflammatory cells to migrate toward the site in the body, such as skin or tissue, where immune challenge has occurred; when such inflammatory cells are prevented from migrating to the site of immune challenge the resulting damage that such cells provide to skin or tissues can be mitigated; (3) the Collagenase Pathway, which is the pathway by which the enzyme collagenase breaks down the peptide bonds in collagen and destroys extracellular structures such as those found in bacteria or infiltrating lymphocytes at the sites of inflammation. The collagenases released will cause tissue damage by breaking down collagen fibrils in the extra cellular matrix; (4) the COX Pathway, which is the pathway by which the cyclooxygenase (COX) enzyme (including but not limited to cyclooxygenase-2 or COX-2) converts arachidonic acid and/or other fatty acids to prostaglandin or prostanoids which ultimately contributes to inflammation or pain in immune challenged tissue such as skin; (5) the Elastase Pathway, which is the pathway by which the enzyme elastase degrades proteins including elastin that are found in bacteria and other molecules. When the Elastase Pathway is triggered the cascade of reactions contributes to inflammation or pain in immune challenged tissue such as skin. Elastase, a peptidase released from infiltrating neutrophils at the site of inflammation, will break down elastin, an elastic fiber that, together with collagen, helps determine the mechanical properties of skin and other tissues. Inhibition of elastase will minimize the damage that may be caused by infiltrating neutrophils which in turn will help preserve the integrity of the extra cellular matrix; (6) the Histamine Pathway, which is the pathway where the amino acid histidine is decarboxylated to form histamine in response to immune challenge or other injury to tissue or skin. Histamine is a biogenic amine that is synthesized and stored in mast cells which reside primarily in the skin. Histamine plays a major role in the initiation of the inflammatory cascade. Upon stimulation, mast cells (and basophils) will release their stored histamine which will bind to H1 receptors on a variety of cells (including smooth muscle cells and endothelial cells in blood vessels) exerting its biologic effects. These effects include vasodilation, separation of endothelial cells (causing abnormal vascular permeability), pain and itching. Inhibition of histamine release provides amelioration from many of the adverse effects of inflammation; (7) the Histamine Receptor Pathway, which is the pathway by which cellular receptors for histamine are activated to bind to histamine, which in turn contributes to the inflammatory condition of tissues or skin; (8) the LO Pathway, which is the pathway by which the enzyme lipooxygenase, preferably 5-lipooxygenase, catalyzes the conversion of arachidonic acid to 5-hydroperoxyeicosatetraenoic acid and then to leukotriene A4, which ultimately contributes to inflammation or pain in immune challenged tissue such as skin; (9) the PDE Pathway, which is the pathway by which PDE (phosphodiesterase) including phosphodiesterase-4 (PDE4) cleaves the phosphodiester bond that may be found in proteins and other molecules present in bacteria, viruses, and other molecules that contribute to skin inflammation. PDE4, in particular, is a member of a family of enzymes that catalyze the degradation of cAMP to the corresponding 5'-nucleotide monophosphate. PDE4 is abundant and is the major regulator of cAMP metabolism in almost every pro-inflammatory and immune cell. PDE4 inhibitors exert their anti-inflammatory effects by inhibiting the breakdown of cAMP (leading to an increased concentration of cAMP in immune cells) which will ulti- mately lead to a decrease in the production and release of pro-inflammatory cytokines such as Interleukin 1-β (IL-1β) and Tumor Necrosis Factor α (TNFα); (10) the PLA-2 Pathway means the pathway by which the phospholipase A2 (PLA-2) enzyme hydrolyzes phospholipids to form fatty acid lysophospholipid products such as arachidonic acid, which ultimately converts to leukotrienes and prostaglandins, which contribute to the inflammatory response in immune challenged tissue such as skin; and (11) the VEGF Pathway, which means the pathway by which VEGF (vascular endothelial growth factor) causes angiogensis (the formation of blood vessels) in immune challenged skin. In addition to inducing angiogenesis, VEGF also is responsible for increasing vascular leakage which will lead to increased edema in damaged tissue or skin.

The term "pathway", when used with respect to inflammation, means a cascade of reactions that occurs when skin or tissue is exposed to immune challenge, and which ultimately contributes to skin inflammation.

One preferred botanical blend comprises a mixture of one or more, preferably all, of the botanicals set forth below:

| Ingredient | Pathway Inhibited | % by weight |
|---|---|---|
| Grapefruit Peel extract | Histamine Pathway | 0.10 |
| Gorgonian Extract | PLA-1 Pathway | 0.50 |
| Nordihydroguaiaretic Acid | 5-LO Pathway | 0.02 |
| Resveratrol | COX-2 Pathway | 0.10 |
| Fucoidan YSK (*Cladosiphon Okamuranus* extract) | Chemotaxis Pathway | 0.10 |
| Polysea PF (Algae extract) | Adhesion Pathway | 0.50 |
| *Siegesbeckia Orientalis* | Collagenase Pathway | 0.20 |
| White Birch extract | Elastase Pathway | 0.10 |
| 18-B-glycerrhetinic acid | PDE Pathway | 0.10 |
| *Magnolia* extract | VEGF Pathway | 0.05 |
| Mangostin or *Garcinia Mangostana* Peel extract (Xanomax ®) | Histamine Receptor Pathway | 0.10 |

In addition, the composition may contain combinations of skin protectant ingredients that permit product marketing claims for treating rash, skin itching, eczema, chapping, windburn, scrapes, cuts, or burns as further defined in 21 C.F.R. §347.20. For example, if the product claims to be useful for treating scrapes, cuts, or burns, may contain two or more of cocoa butter, cod liver oil, hard fat, lanolin, mineral oil, petrolatum, and white petrolatum in the amounts specified under the "E. Skin Protectant" category as set forth herein. If the product claims to be useful for treating chafed, chapped, or cracked skin or the effects of wind or cold weather the formula may contain two or more of allantoin, cocoa butter, cod liver oil, dimethicone, glycerin, hard fat, lanolin, mineral oil, petrolatum, and white petrolatum in the amounts specified under the "E. Skin Protectant" category as set forth herein. If the product claims to be useful for treating minor skin irritation, the composition may contain starch in the amounts specified under the "E. Skin Protectant" category as set forth herein. If the product claims to be useful for treating minor skin irritation due to rashes or eczema it may contain colloidal oatmeal and/or mineral oil in the amounts specified under the "E. Skin Protectant" category as set forth herein.

J. Skin Whitening Ingredients

It may also be desirable to incorporate one or more ingredients that are known to be skin whitening ingredients into the composition. The whitening ingredients may act in a variety of ways, for example, they may be tyrosinase inhibitors, or have an effect on another portion of the cellular pathway involved when melanocytes form pigment in skin. If present, such whitening agents may range from about 0.001 to 45% of the composition. The skin whiteners may be those known as "quasi-drug" ingredients in Japan. Examples of skin whitening ingredients include but are not limited to linoleic acid, cyclohexadecanol, Phytolight® (a mixture of apple extract, cucumber extract, *Scutellaria Baicalensis* extract, and green tea extract), Phytowhite® (a mixture of *Scutellaria Baicalensis* extract, *Pyrus Malus* extract, and *Cucumis Sativus* extract), glabridin, Vitamin C or its derivatives, licorice extract or its derivatives, ascorbyl tetraisopalmitate, ubiquionone, green tea extract, gentian extract, Mulberry extract, *Scutellaria* extract, zinc glycinate, Black Tea extract, Arnica extract, Swertia extract, Magnolignan (5,5-dipropyl-biphenyl-2,2-diol), Arbutin, kojic acid, Rucinol, ellagic acid, t-AMCHA (trans-4(aminomethyl)cyclohexane carboxylic acid)), azealic acid, and so on. Any skin whitening ingredient may be suitable, whether quasi-drug approved or not, so long as the ingredient has the effect of whitening skin.

In one preferred embodiment the composition is substantially free of one or more of talc, paraben preservatives, fragrance, and/or oil (mineral oil). The term "substantially free of" means that the ingredient is present in an amount small enough that it does not need to be listed on the ingredient label in accordance with 21 C.F.R. Chapter I, Part 701, hereby incorporated by reference in its entirety.

The invention will be further described in connection with the following examples which are set forth for the purposes of illustration only.

EXAMPLE 1

A loose powder composition was prepared as follows:

| Ingredients | w/w % |
| --- | --- |
| Oat flour | QS 100 |
| Titanium dioxide/aluminum hydroxide (98:2) | 20.00 |
| Mica | 15.08 |
| *Glycine Soja* (Soybean) flour | 9.99 |
| Mica | 4.93 |
| Titanium dioxide | 4.50 |
| Tapioca Starch/water (90:10) | 4.00 |
| Silica | 3.00 |
| Shea butter (*Butyrospermum Parkii*) | 3.00 |
| Octyldodecyl stearoyl stearate | 1.80 |
| Titanium dioxide/silica/mica (50:40:10) | 1.40 |
| Isostearyl neopentanoate | 1.197 |
| Yellow iron oxides/triethoxycaprylylsilane (90:10) | 1.08 |
| Dimethicone | 1.00 |
| Bismuth oxychloride/silica/mica (70:15:15) | 1.00 |
| Rice starch/dimethicone (95:5) | 1.00 |
| Kaolin | 0.50 |
| Red iron oxides/triethoxycaprylylsilxane (99:1) | 0.42 |
| Black iron oxides/triethoxycaprylylsilane (99:1) | 0.33 |
| Chlorophenesin | 0.30 |
| Potassium sorbate | 0.20 |
| Tocopheryl acetate | 0.10 |
| Ascorbyl palmitate | 0.20 |

-continued

| Ingredients | w/w % |
| --- | --- |
| Squalane/*Hordeum Vulgare* (barley) extract/ *Triticum Vulgare* (Wheat) Germ extract (75:15:10) | 0.10 |
| *Lycium Chinense* Fruit Extract/maltodextrin (90:10) | 0.05 |
| *Punica Granatum* sterols | 0.05 |

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A pigmented face powder composition containing less than 5% by weight of water, free of talc, fragrance, mineral oil and parabens, wherein the particulate phase comprises iron oxide pigments, silica, titanium dioxide, mica; and a non-synthetic mixture of natural edible grains consisting of oat flour, soybean flour, tapioca starch and rice starch with particle sizes of the mixture of edible grains ranging from 1 to 50 microns in diameter.

2. The composition of claim 1 wherein at least one of the edible grains is a certified organic grain and the powder composition contains containing less than 3% by weight of the total composition of water.

3. The composition of claim 1 wherein the powder is non-comedogenic and/or non-acnegenic.

4. The composition of claim 1 further comprising zinc oxide.

5. The powder composition of claim 1 formulated into a water and oil emulsion.

6. The composition of claim 1 further comprising a botanical extract from *Lycium*, *Punica*, or mixtures thereof.

7. The composition of claim 6 wherein the *Lycium* extract is *Lycium chinensis* and the *Punica* extract is *Punica granatum*.

8. A pigmented face powder composition containing less than 3% by weight of water, and free of talc, mineral oil, fragrance and parabens, comprising a particulate phase containing iron oxide pigments, titanium dioxide, and a non-synthetic mixture of natural edible grains consisting of oat flour, soybean flour, tapioca starch and rice starch wherein the mixture of edible grains have particle sizes of 1 to 50 microns.

9. The powder composition of claim 8 further comprising a botanical extract from *Lycium*, *Punica*, or mixtures thereof.

10. The powder composition of claim 9 where the *Lycium* extract is from *Lycium chinensis*.

11. The powder composition of claim 9 wherein the *Punica* extract is from *Punica granatum*.

12. A method for protecting and relieving undesirable effects of injured or exposed skin or mucous membrane surfaces from harmful or annoying stimuli comprising applying to the skin or mucous membranes the powder composition of claim 1.

13. The method of claim 12 wherein the composition is applied to facial skin.

* * * * *